United States Patent
Arola et al.

(10) Patent No.: US 12,271,543 B2
(45) Date of Patent: *Apr. 8, 2025

(54) CONTROLLER WITH BIOMETRIC SENSOR PATTERN

(71) Applicant: Microsoft Technology Licensing, LLC, Redmond, WA (US)

(72) Inventors: Joni Arola, Tampere (FI); Aki Vänninen, Tampere (FI)

(73) Assignee: Microsoft Technology Licensing, LLC, Redmond, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/146,635

(22) Filed: Dec. 27, 2022

(65) Prior Publication Data

US 2023/0136964 A1 May 4, 2023

Related U.S. Application Data

(63) Continuation of application No. 14/931,142, filed on Nov. 3, 2015, now Pat. No. 11,537,224.

(51) Int. Cl.
| | |
|---|---|
| *G06F 3/041* | (2006.01) |
| *A61B 5/00* | (2006.01) |
| *A61B 5/1172* | (2016.01) |
| *G06F 1/16* | (2006.01) |
| *G06V 40/10* | (2022.01) |
| *G06V 40/13* | (2022.01) |

(52) U.S. Cl.
CPC ............ *G06F 3/041* (2013.01); *A61B 5/1172* (2013.01); *A61B 5/6898* (2013.01); *G06F 1/1637* (2013.01); *G06F 3/0412* (2013.01); *G06V 40/10* (2022.01); *G06V 40/1329* (2022.01); *A61B 5/7235* (2013.01); *A61B 2560/0462* (2013.01); *A61B 2562/166* (2013.01); *G06F 2200/1635* (2013.01); *G06F 2203/04102* (2013.01); *G06V 40/15* (2022.01)

(58) Field of Classification Search
CPC ...... G06F 3/041; G06F 1/1637; G06F 3/0412; G06F 2200/1635; G06F 2203/04102; A61B 5/1172; A61B 5/6898; A61B 5/7235; A61B 2560/0462; A61B 2562/166; G06V 40/10; G06V 40/1329; G06V 40/15

See application file for complete search history.

(56) References Cited

U.S. PATENT DOCUMENTS

| | | | | |
|---|---|---|---|---|
| 6,289,114 B1 * | 9/2001 | Mainguet | ............ | G06V 40/1335 382/284 |
| 9,880,676 B1 * | 1/2018 | Mukherjee | ............ | G06F 3/0447 |
| 2003/0222857 A1 * | 12/2003 | Abileah | ............... | G02F 1/13338 345/173 |

(Continued)

*Primary Examiner* — Patrick N Edouard
*Assistant Examiner* — Joseph P Fox
(74) *Attorney, Agent, or Firm* — Barta Jones, PLLC

(57) ABSTRACT

In one example, a display unit comprises a display panel that is configured to display digital images. The display unit further comprises an at least partially transparent protective layer that is arranged above the display panel. The display unit further comprises a controller that is communicatively attached onto an upper surface of the display panel. A biometric sensor pattern is integrated in the controller, and the controller is configured to control the biometric sensor pattern.

20 Claims, 10 Drawing Sheets

(56) References Cited

U.S. PATENT DOCUMENTS

| | | | |
|---|---|---|---|
| 2011/0267298 A1* | 11/2011 | Erhart | G06F 21/32 |
| | | | 345/173 |
| 2013/0272586 A1* | 10/2013 | Russo | G06V 40/12 |
| | | | 382/124 |
| 2014/0140588 A1* | 5/2014 | Chou | G06V 40/1306 |
| | | | 382/124 |
| 2015/0030217 A1* | 1/2015 | Wickboldt | G06F 3/0443 |
| | | | 382/124 |
| 2015/0109214 A1* | 4/2015 | Shi | G06F 3/04166 |
| | | | 345/173 |
| 2017/0024597 A1* | 1/2017 | Cho | G09G 3/36 |

* cited by examiner

CONTROLLER WITH BIOMETRIC SENSOR PATTERN

CROSS-REFERENCE TO RELATED APPLICATION

This application claims priority to U.S. Non-Provisional patent application Ser. No. 14/931,142, entitled "CONTROLLER WITH BIOMETRIC SENSOR PATTERN," filed on Nov. 3, 2015, the disclosure of which is incorporated herein by reference in its entirety.

BACKGROUND

Biometric sensors, such as fingerprint sensors are becoming common in various electronic devices, including mobile communication devices. As a result, there may be instances when a separate biometric sensor takes space from other components and adds complexity to implementation.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one example, a display unit comprises a display panel that is configured to display digital images. The display unit further comprises an at least partially transparent protective layer that is arranged above the display panel. The display unit further comprises a controller that is communicatively attached onto an upper surface of the display panel. A biometric sensor pattern is integrated in the controller, and the controller is configured to control the biometric sensor pattern.

In another example, an electronic device and a sensor controller have been discussed along with the features of the display unit.

Many of the attendant features will be more readily appreciated as the same becomes better understood by reference to the following detailed description considered in connection with the accompanying drawings.

DESCRIPTION OF THE DRAWINGS

The present description will be better understood from the following detailed description read in light of the accompanying drawings, wherein.

Like reference numerals are used to designate like parts in the accompanying drawings.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Figure 1:
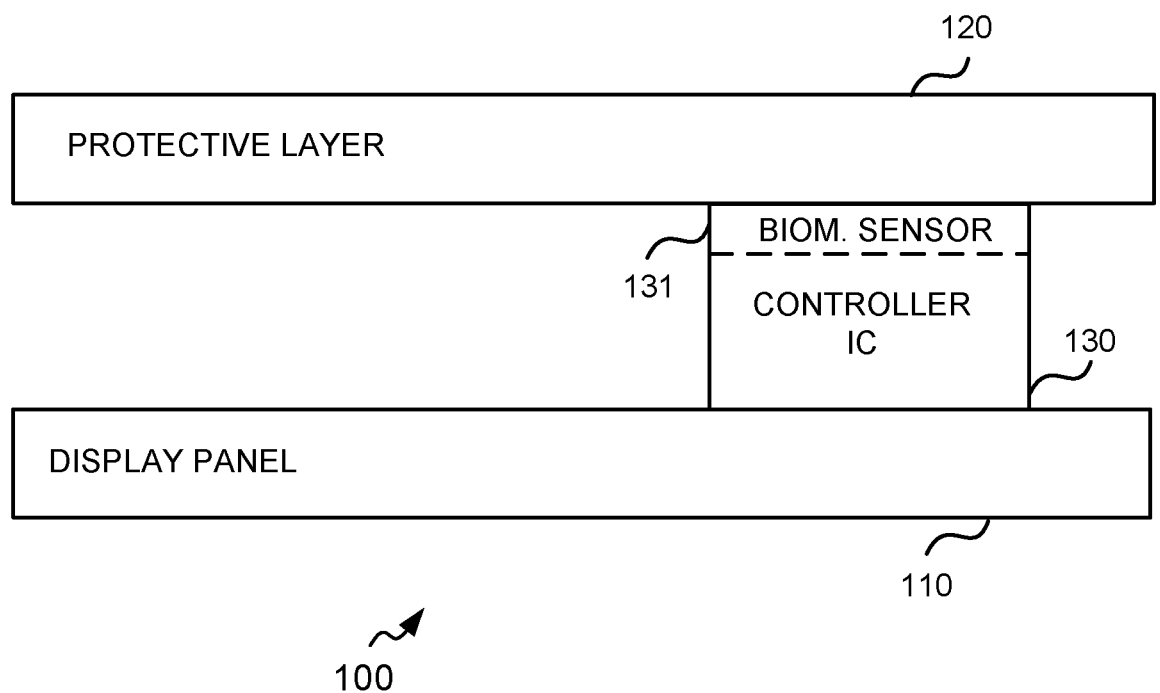
FIG. 1 is an example block diagram of a display unit in accordance with an example embodiment.

FIG. 1 illustrates a display unit 100 in accordance with an example embodiment. The display unit 100 may be employed, for example, in the electronic device 900 of FIG. 9 or the apparatus 1000 of FIG. 10. However, it should be noted that the display unit 100 may also be employed on a variety of other devices and apparatuses, and therefore, embodiments should not be limited to application on devices and apparatuses such as the electronic device 900 of FIG. 9 and the apparatus 1000 of FIG. 10. Furthermore, it should be noted that at least some of the elements described below may not be mandatory and thus some may be omitted in certain embodiments.

The display unit 100 comprises a display panel 110 that is configured to display digital images. The display unit 100 further comprises an at least partially transparent protective layer 120 that is arranged above the display panel 110, such that the digital images displayed by the display panel 110 are visible through the at least partially transparent protective layer 120, and the at least partially transparent protective layer 120 protects the display panel 110 e.g. against wear and tear, impacts, and the like. The display unit 100 further comprises a controller 130 that is communicatively attached onto an upper surface of the display panel 110. Herein, the "upper" surface of the display panel 110 refers to the surface of the display panel 110 that faces the at least partially transparent protective layer 120. Herein, the "communicatively" attached refers to an attachment enabling routing of signals (such as control signals and the like) via the display panel 110. A biometric sensor pattern 131 is integrated in the controller 130, and the controller 130 is configured to control the biometric sensor pattern 131. In the example embodiment of FIG. 1, the controller 130 may be further arranged below the at least partially transparent protective layer 120, and more particularly between the at least partially transparent protective layer 120 and the display panel 110. Herein, the term "at least partially transparent" refers to the protective layer 120 being transparent enough to allow biometric sensing to work through it (in embodiments in which the protective layer 120 covers the biometric sensor pattern 131) and to allow viewing the digital images displayed by the display panel 110 through it. The protective layer 120 may include e.g. text and/or graphics and the like as long as they do not substantially interfere with the biometric sensing and the viewing of the digital images.

The biometric sensor pattern 131 may be integrated on the upper surface of the controller 130 or at least partly inside the upper surface of the controller 131. Herein, the "upper" surface of the controller 130 refers to the surface of the controller 130 that is furthest from the surface of the controller 130 attached to the display panel 110. The biometric sensor pattern 131 may comprise at least a fingerprint sensor pattern and/or a pulse sensor pattern. The fingerprint sensor pattern may comprise e.g. capacitive sensing electrodes arranged in a pattern having a suitably high pitch or resolution to allow fingerprint sensing.

The controller 130 (or its body) and the biometric sensor pattern 131 may comprise semiconductor material, such as silicon. The controller 130 may comprise an integrated circuit (IC). The controller 130 may be further configured to control the display panel 110 in which case the controller 130 may comprise e.g. a display driver IC (DDI). Alternatively, the display unit 100 may comprise an additional controller (not shown in FIG. 1) configured to control the display panel 110.

The display unit 100 may comprise e.g. one of a liquid-crystal display (LCD) unit, an organic light-emitting diode (OLED) display unit, and an electrophoretic ink (E Ink) display unit. The at least partially transparent protective layer 120 may comprise e.g. any suitable glass, plastic, film, ceramic, or flexible material.

The biometric sensor pattern 131 is utilized to sense one or more predefined biometric properties of an external object (such as a fingertip of a user) placed against the biometric sensor pattern 131. For embodiments in which the at least partially transparent protective layer 120 covers the biometric sensor pattern 131, properties, such as thickness and material of the at least partially transparent protective layer 120 (and any optional additional layers between the at least partially transparent protective layer 120 and the biometric sensor pattern 131) are selected such that they do not obstruct achieving these sensing objectives of the biometric sensor pattern 131. In an embodiment, the display panel 110 may comprise flexible material.

Figure 2:
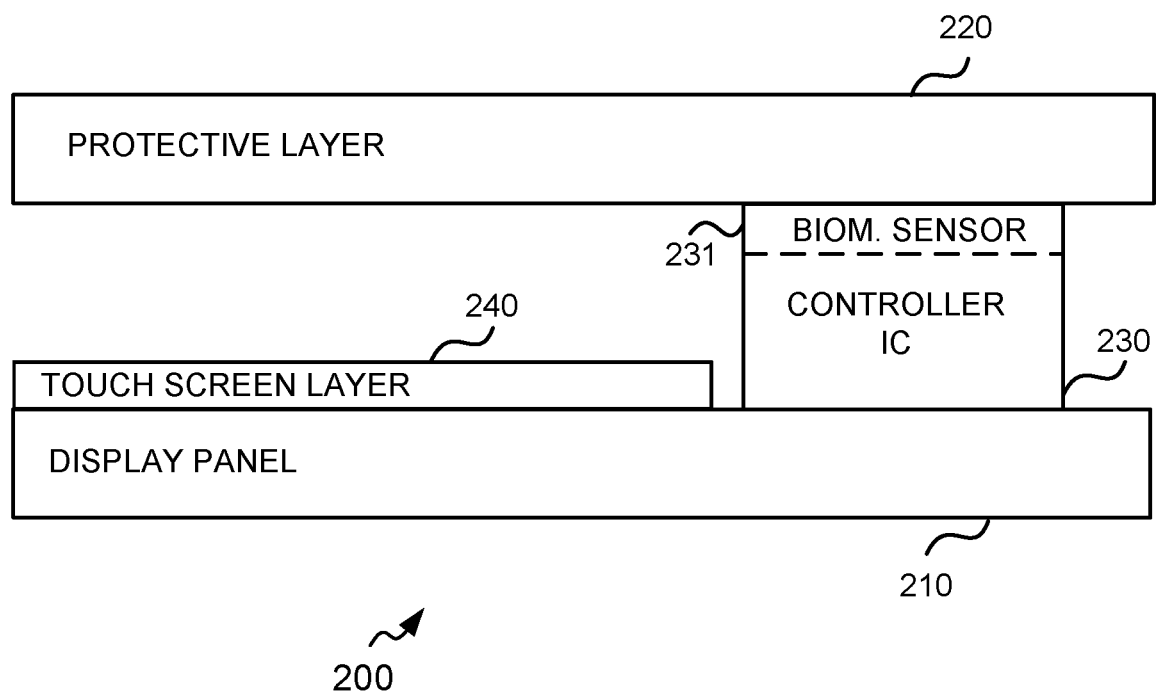
FIG. 2 is an example block diagram of a display unit in accordance with an example embodiment.

FIG. 2 illustrates a display unit 200 in accordance with an example embodiment. The display unit 200 may be employed, for example, in the electronic device 900 of FIG. 9 or the apparatus 1000 of FIG. 10. However, it should be noted that the display unit 200 may also be employed on a variety of other devices and apparatuses, and therefore, embodiments should not be limited to application on devices and apparatuses such as the electronic device 900 of FIG. 9 and the apparatus 1000 of FIG. 10. Furthermore, it should be noted that at least some of the elements described below may not be mandatory and thus some may be omitted in certain embodiments.

In the example of FIG. 2, the functionalities and properties of the display panel 210, the at least partially transparent protective layer 220, the controller 230, and the biometric sensor pattern 231 are substantially similar to those of their counterparts in the example of FIG. 1, so their descriptions are not repeated here in detail.

The example of FIG. 2 further comprises a touch screen layer 240 that is arranged aside the controller 230 and above the display panel 210, e.g. between the display panel 210 and the at least partially transparent protective layer 220. In an embodiment, the touch screen layer 240 may comprise flexible material. In an embodiment, the touch screen layer 240 may comprise e.g. capacitive, resistive or inductive sensing electrodes arranged in a pattern having a suitably high pitch or resolution to allow touch sensing.

The location of the touch screen layer 240 in FIG. 2 illustrates an example for deploying the touch screen layer (also known as on-cell type of touch). Other examples may include e.g. deploying the touch screen layer integrated in the display panel 210 (also known as in-cell type of touch), and deploying the touch screen layer as one layer on top of the display panel 210 and one layer integrated in the display panel 210 (also known as hybrid type of touch).

Similar to the embodiment of FIG. 1, the controller 230 is configured to control the biometric sensor pattern 231. The controller 230 may be further configured to control the display panel 210 in which case the controller 230 may comprise e.g. a display driver IC (DDI). Alternatively, the controller 230 may be further configured to control touch screen layer 240 in which case the controller 230 may comprise a touch driver IC. Alternatively, the controller 230 may be further configured to control both the display panel 210 and the touch screen layer 240 in which case the controller 230 may comprise e.g. a touch and display driver IC (TDDI). Alternatively, the display unit 200 may comprise one or more additional controllers (not shown in FIG. 2) configured to control the display panel 210 and/or the touch screen layer 240.

Figure 3:
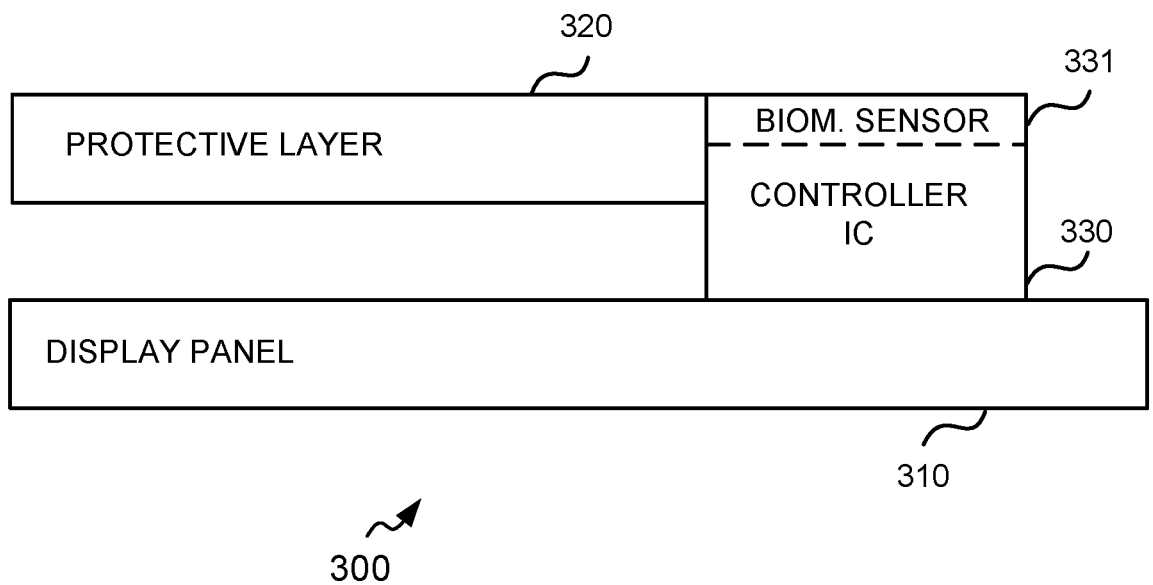
FIG. 3 is an example block diagram of a display unit in accordance with an example embodiment.

FIG. 3 illustrates a display unit 300 in accordance with an example embodiment. The display unit 300 may be employed, for example, in the electronic device 900 of FIG. 9 or the apparatus 1000 of FIG. 10. However, it should be noted that the display unit 300 may also be employed on a variety of other devices and apparatuses, and therefore, embodiments should not be limited to application on devices and apparatuses such as the electronic device 900 of FIG. 9 and the apparatus 1000 of FIG. 10. Furthermore, it should be noted that at least some of the elements described below may not be mandatory and thus some may be omitted in certain embodiments.

In the example of FIG. 3, the functionalities and properties of the display panel 310, the at least partially transparent protective layer 320, the controller 330, and the biometric sensor pattern 331 are substantially similar to those of their counterparts in the examples of FIG. 1 and FIG. 2, so their descriptions are not repeated here in detail. The example of FIG. 3 may further comprise a touch screen layer similar to the touch screen layer 240 of FIG. 2 that is arranged aside the controller 330 and above the display panel 310, e.g. between the display panel 310 and the at least partially transparent protective layer 320, even though it is not explicitly shown in FIG. 3.

In the example of FIG. 3, the controller 330 is further arranged below the at least partially transparent protective layer 320, such that the at least partially transparent protective layer 320 does not directly cover the controller 330. E.g. an additional protective layer or film (not shown in FIG. 3) may be arranged to directly cover the controller 330.

Figure 4:
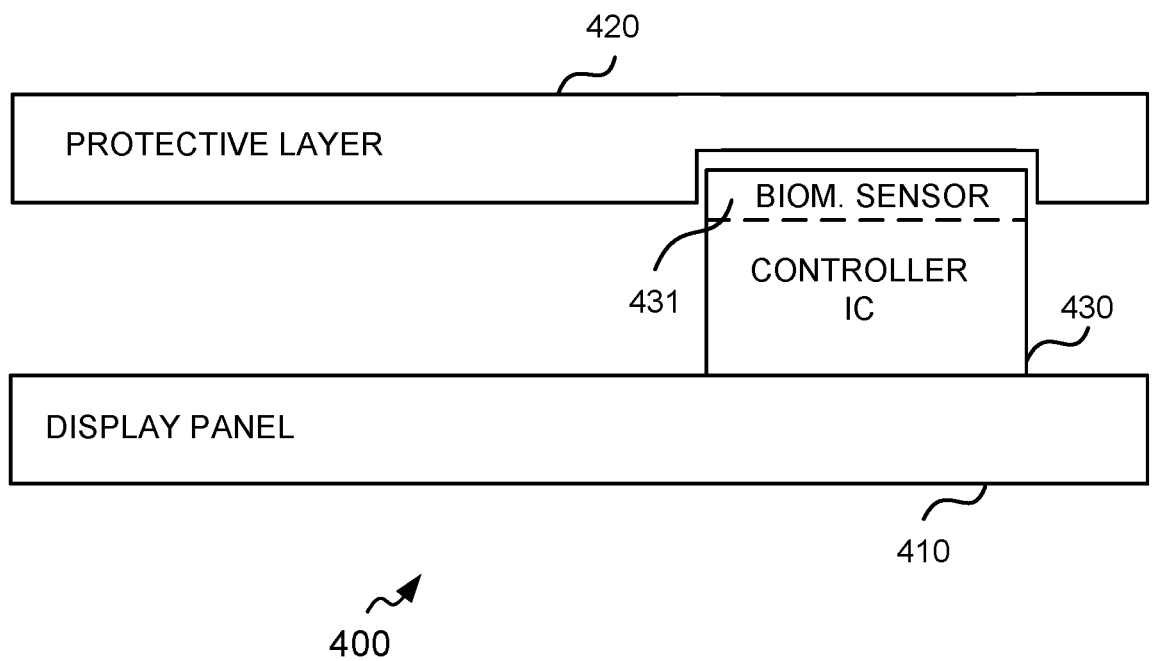
FIG. 4 is an example block diagram of a display unit in accordance with an example embodiment.

FIG. 4 illustrates a display unit 400 in accordance with an example embodiment. The display unit 400 may be employed, for example, in the electronic device 900 of FIG. 9 or the apparatus 1000 of FIG. 10. However, it should be noted that the display unit 400 may also be employed on a variety of other devices and apparatuses, and therefore, embodiments should not be limited to application on devices and apparatuses such as the electronic device 900 of FIG. 9 and the apparatus 1000 of FIG. 10. Furthermore, it should be noted that at least some of the elements described below may not be mandatory and thus some may be omitted in certain embodiments.

In the example of FIG. 4, the functionalities and properties of the display panel 410, the at least partially transparent protective layer 420, the controller 430, and the biometric sensor pattern 431 are substantially similar to those of their counterparts in the examples of FIG. 1-FIG. 3, so their descriptions are not repeated here in detail. The example of FIG. 4 may further comprise a touch screen layer similar to the touch screen layer 240 of FIG. 2 that is arranged aside the controller 430 and above the display panel 410, e.g. between the display panel 410 and the at least partially transparent protective layer 420, even though it is not explicitly shown in FIG. 4.

In the example of FIG. 4, the at least partially transparent protective layer 420 comprises a recess in its lower surface configured to receive the controller 430 and the biometric sensor pattern 431 at least partly.

Figure 5:
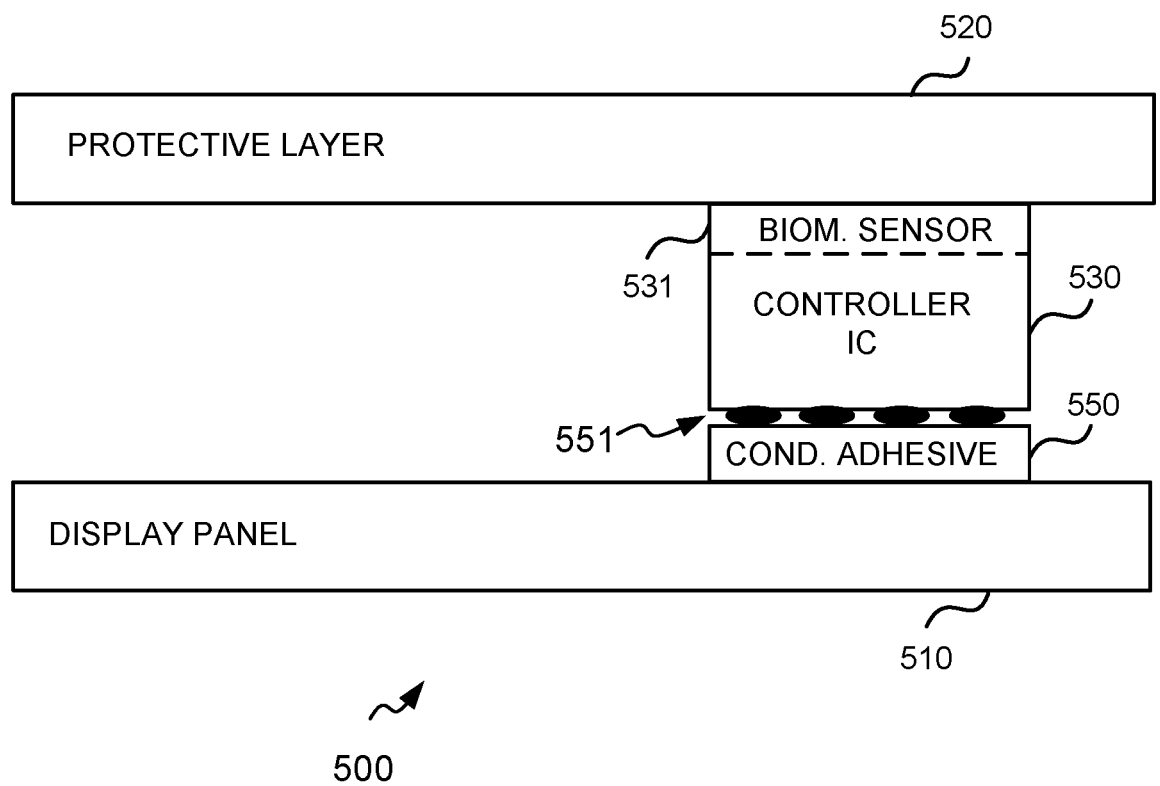
FIG. 5 is an example block diagram of a display unit in accordance with an example embodiment.

FIG. 5 illustrates a display unit 500 in accordance with an example embodiment. The display unit 500 may be employed, for example, in the electronic device 900 of FIG. 9 or the apparatus 1000 of FIG. 10. However, it should be noted that the display unit 500 may also be employed on a variety of other devices and apparatuses, and therefore, embodiments should not be limited to application on devices and apparatuses such as the electronic device 900 of FIG. 9 and the apparatus 1000 of FIG. 10. Furthermore, it should be noted that at least some of the elements described below may not be mandatory and thus some may be omitted in certain embodiments.

In the example of FIG. 5, the functionalities and properties of the display panel 510, the at least partially transparent protective layer 520, the controller 530, and the biometric sensor pattern 531 are substantially similar to those of their counterparts in the examples of FIG. 1-FIG. 4, so their descriptions are not repeated here in detail. The example of FIG. 5 may further comprise a touch screen layer similar to the touch screen layer 240 of FIG. 2 that is arranged aside the controller 530 and above the display panel 510, e.g. between the display panel 510 and the at least partially transparent protective layer 520, even though it is not explicitly shown in FIG. 5.

The example of FIG. 5 details an example of providing the communicative attachment of the controller 530 onto the upper surface of the display panel 510. The controller 530 is communicatively attached onto the upper surface of the display panel 510 via at least one of a conductive adhesive layer 550 that is arranged between the upper surface of the display panel 510 and a lower surface of the controller 530, and multiple conductive bonding points 551 that are arranged on the lower surface of the controller 530. The conductive adhesive layer 550 may comprise e.g. a layer of anisotropic conductive film (ACF). A similar arrangement may be used at least in any of the examples of FIGS. 1-4 and 6-10.

Figure 6:
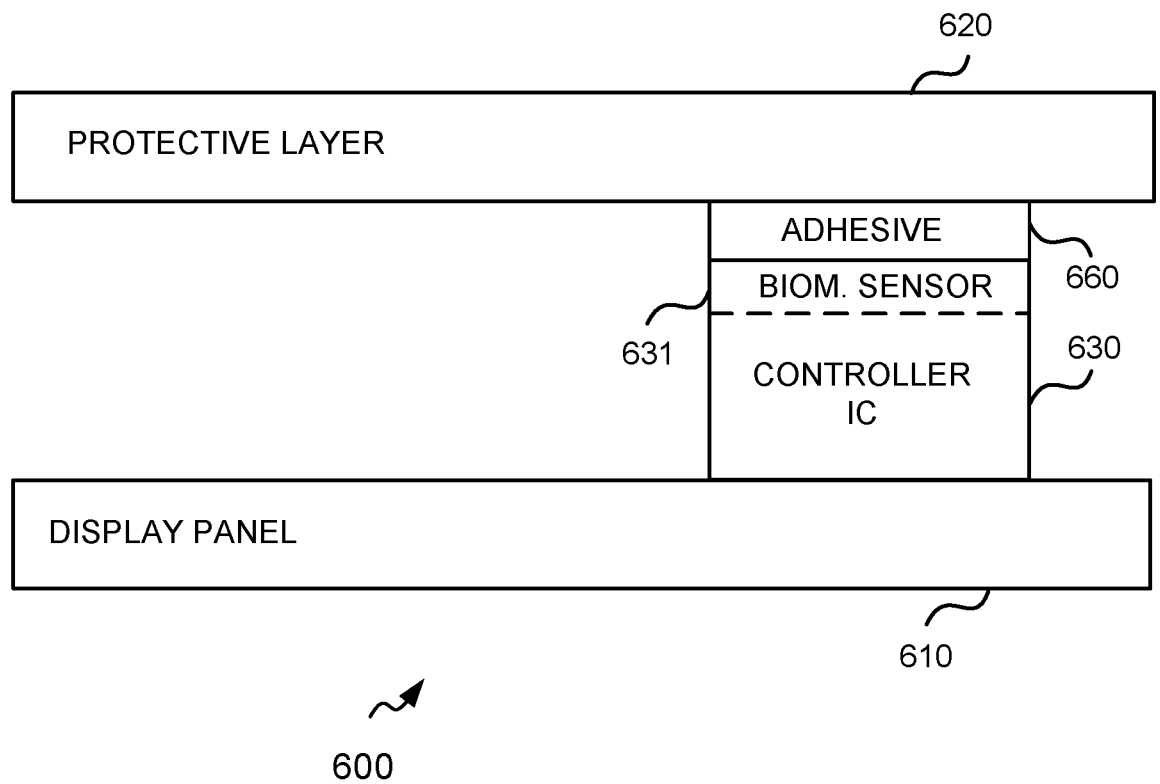
FIG. 6 is an example block diagram of a display unit in accordance with an example embodiment.

FIG. 6 illustrates a display unit 600 in accordance with an example embodiment. The display unit 600 may be employed, for example, in the electronic device 900 of FIG. 9 or the apparatus 1000 of FIG. 10. However, it should be noted that the display unit 600 may also be employed on a variety of other devices and apparatuses, and therefore, embodiments should not be limited to application on devices and apparatuses such as the electronic device 900 of FIG. 9 and the apparatus 1000 of FIG. 10. Furthermore, it should be noted that at least some of the elements described below may not be mandatory and thus some may be omitted in certain embodiments.

In the example of FIG. 6, the functionalities and properties of the display panel 610, the at least partially transparent protective layer 620, the controller 630, and the biometric sensor pattern 631 are substantially similar to those of their counterparts in the examples of FIG. 1-FIG. 5, so their descriptions are not repeated here in detail. The example of FIG. 6 may further comprise a touch screen layer similar to the touch screen layer 240 of FIG. 2 that is arranged aside the controller 630 and above the display panel 610, e.g. between the display panel 610 and the at least partially transparent protective layer 620, even though it is not explicitly shown in FIG. 6.

In the example of FIG. 6, the controller 630 with the biometric sensor pattern 631 is attached to the lower surface of the at least partially transparent protective layer 620 via an adhesive layer or film 660 arranged between the lower surface of the at least partially transparent protective layer 620 and an upper surface of the controller 630. A similar arrangement may be used at least in any of the examples of FIGS. 1-5, 7 and 9-10.

Figure 7:
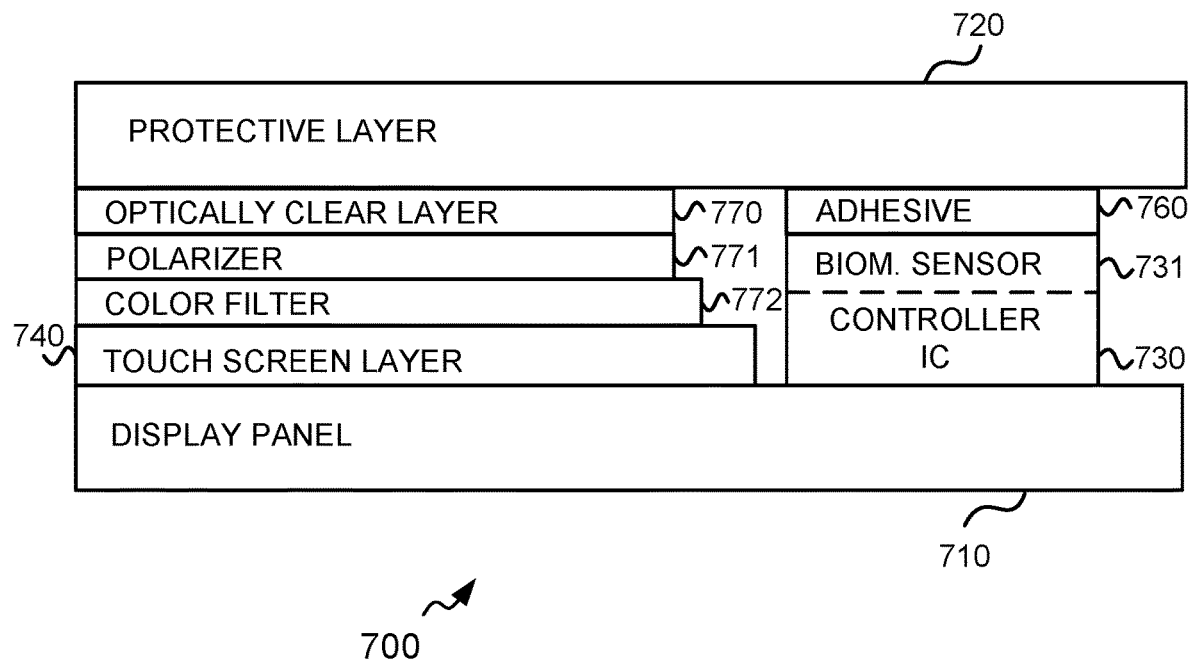
FIG. 7 is an example block diagram of a display unit in accordance with an example embodiment.

FIG. 7 illustrates a display unit 700 in accordance with an example embodiment. The display unit 700 may be employed, for example, in the electronic device 900 of FIG. 9 or the apparatus 1000 of FIG. 10. However, it should be noted that the display unit 700 may also be employed on a variety of other devices and apparatuses, and therefore, embodiments should not be limited to application on devices and apparatuses such as the electronic device 900 of FIG. 9 and the apparatus 1000 of FIG. 10. Furthermore, it should be noted that at least some of the elements described below may not be mandatory and thus some may be omitted in certain embodiments.

In the example of FIG. 7, the functionalities and properties of the display panel 710, the at least partially transparent protective layer 720, the controller 730, the biometric sensor pattern 731, the touch screen layer 740 and the adhesive layer or film 760 are substantially similar to those of their counterparts in the examples of FIG. 1-FIG. 6, so their descriptions are not repeated here in detail.

The example of FIG. 7 further illustrates an example structure of an LCD type the display unit 700. The display unit 700 further comprises an optically clear layer 770 that is arranged between the at least partially transparent protective layer 720 and the display panel 710. The optically clear layer 770 may comprise e.g. optically clear resin (OCR) and/or optically clear adhesive (OCA). In an embodiment, the optically clear layer 770 may comprise an air gap or the like. The display unit 700 may further comprise a polarizer 771 that is arranged between the at least partially transparent protective layer 720 and the display panel 710 and configured to direct light emitting from the display panel 710. The display unit 700 may further comprise a color filter 772 that is arranged between the at least partially transparent protective layer 720 and the display panel 710 and configured to adjust the visible color saturation of the display panel 710.

Figure 8:
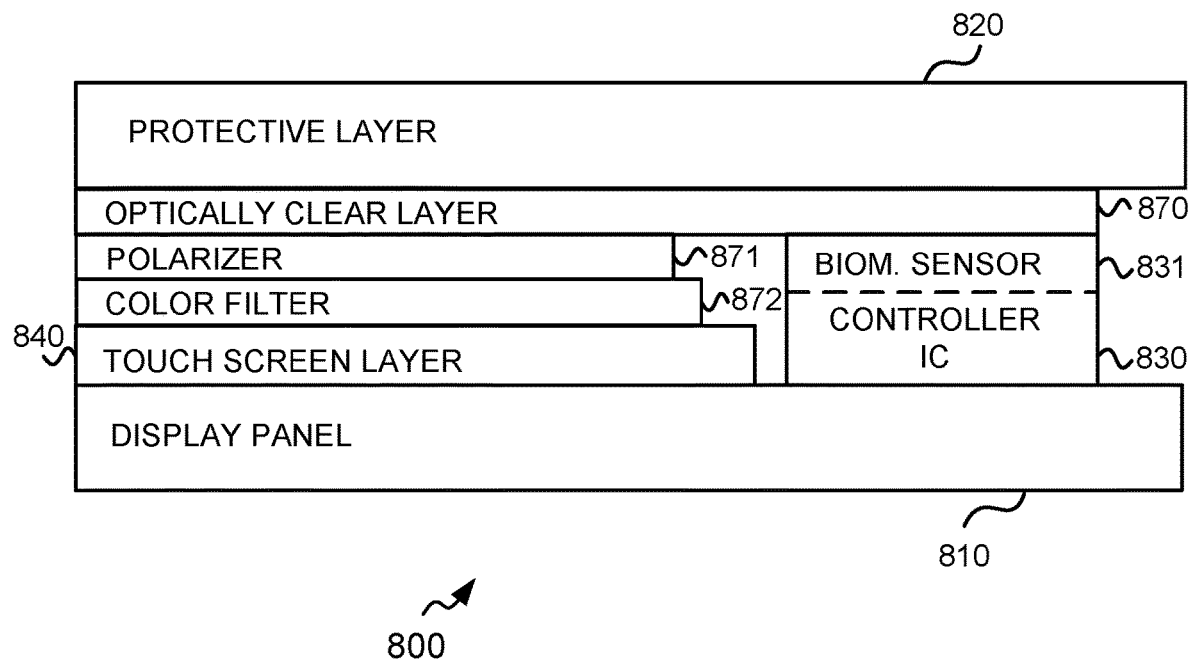
FIG. 8 is an example block diagram of a display unit in accordance with an example embodiment.

FIG. 8 illustrates a display unit 800 in accordance with an example embodiment. The display unit 800 may be employed, for example, in the electronic device 900 of FIG. 9 or the apparatus 1000 of FIG. 10. However, it should be noted that the display unit 800 may also be employed on a variety of other devices and apparatuses, and therefore, embodiments should not be limited to application on devices and apparatuses such as the electronic device 900 of FIG. 9 and the apparatus 1000 of FIG. 10. Furthermore, it should be noted that at least some of the elements described below may not be mandatory and thus some may be omitted in certain embodiments.

In the example of FIG. 8, the functionalities and properties of the display panel 810, the at least partially transparent protective layer 820, the controller 830, the biometric sensor pattern 831, the touch screen layer 840, the polarizer 871, and the color filter 872 are substantially similar to those of their counterparts in the examples of FIG. 1-FIG. 7, so their descriptions are not repeated here in detail.

In the example of FIG. 8, the display unit 800 further comprises an optically clear layer 870 that is arranged between the at least partially transparent protective layer 820 and the display panel 810. The optically clear layer 870 may comprise e.g. optically clear resin (OCR) and/or optically clear adhesive (OCA). In the example of FIG. 8, the optically clear layer 870 extends between the lower surface of the at least partially transparent protective layer 820 and an upper surface of the controller 830 with the biometric sensor pattern 831.

Figure 9:
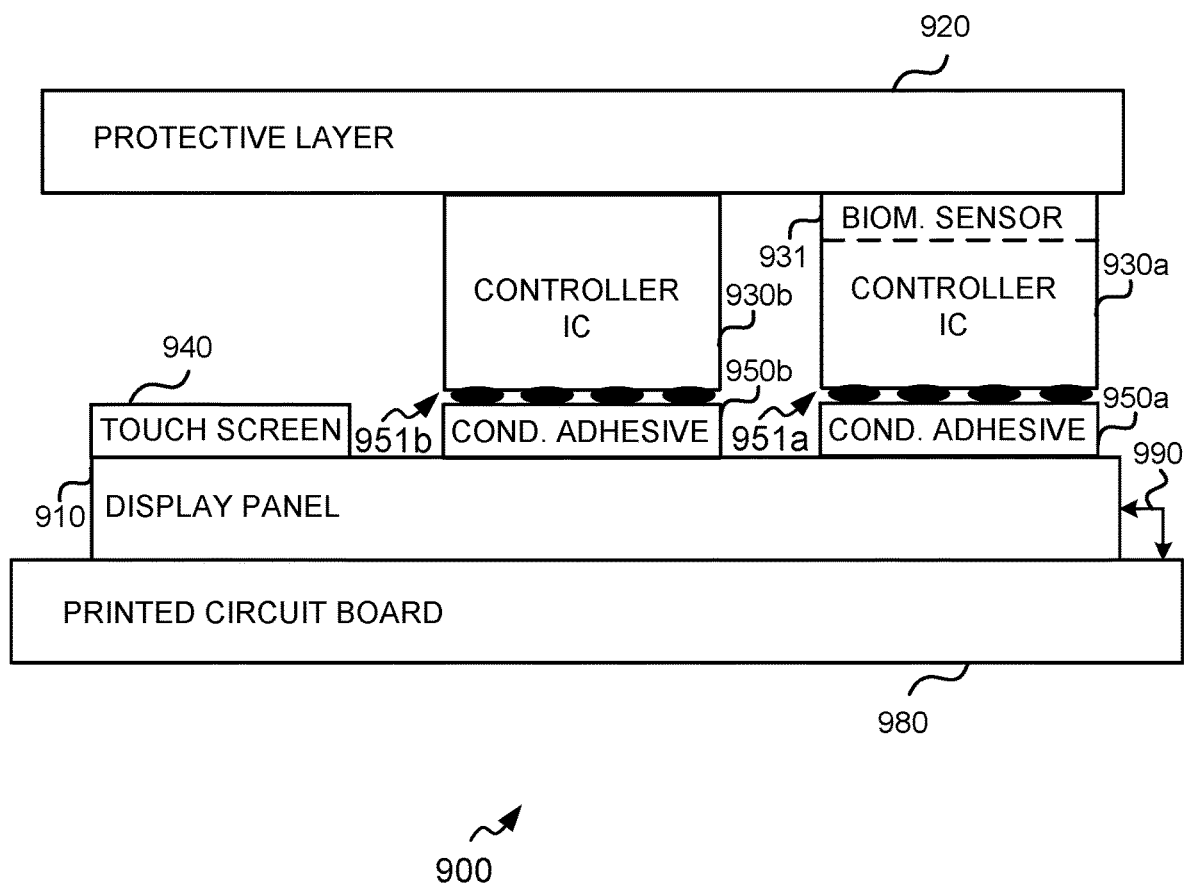
FIG. 9 is an example block diagram of an electronic device in accordance with an example embodiment.

FIG. 9 is an example block diagram of an electronic device 900 in accordance with an example embodiment. The electronic device 900 may comprise e.g. a display unit 100 of FIG. 1, a display unit 200 of FIG. 2, a display unit 300 of FIG. 3, a display unit 400 of FIG. 4, a display unit 500 of FIG. 5, a display unit 600 of FIG. 6, a display unit 700 of FIG. 7, or a display unit 800 of FIG. 8. It should be noted that at least some of the elements described below may not be mandatory and thus some may be omitted in certain embodiments.

In the example of FIG. 9, the functionalities and properties of the display panel 910, the at least partially transparent protective layer 920, the controllers 930*a*, 930*b*, the biometric sensor pattern 931, the touch screen layer 940, the conductive adhesive layers 950*a*, 950*b*, and the conductive bonding points 951*a*, 951*b* are substantially similar to those of their counterparts in the examples of FIG. 1-FIG. 8, so their descriptions are not repeated here in detail.

The electronic device 900 further comprises a printed circuit board 980 that is arranged such that at least a part of the display panel 910 is located above the printed circuit board 980. In the example of FIG. 9, a single connector 990 connects the display panel 910 and the printed circuit board 980 to communicate e.g. the signals routed from/to the controllers 930*a*, 930*b* via the conductive adhesive layers 950*a*, 950*b* and the conductive bonding points 951*a*, 951*b*.

Figure 10:
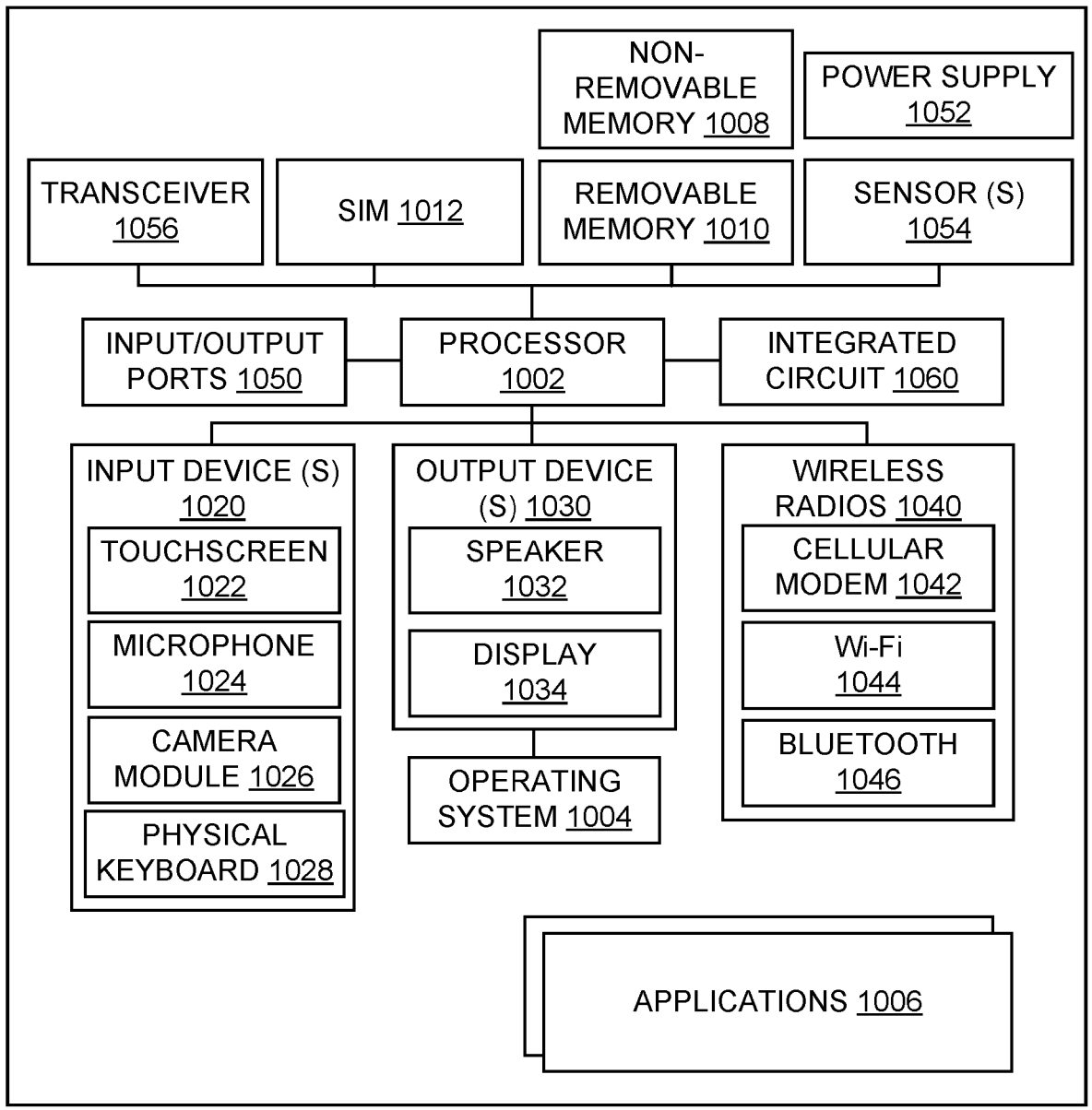
FIG. 10 illustrates an example block diagram of an apparatus capable of implementing example embodiments described herein.

FIG. 10 is a schematic block diagram of an apparatus 1000 capable of implementing embodiments of the techniques described herein. It should be understood that the apparatus 1000 as illustrated and hereinafter described is merely illustrative of one type of apparatus or an electronic device and should not be taken to limit the scope of the embodiments. As such, it should be appreciated that at least some of the components described below in connection with the apparatus 1000 may be optional and thus in an example embodiment may include more, less or different components than those described in connection with the example embodiment of FIG. 10. As such, among other examples, the apparatus 1000 could be any of apparatuses utilizing a biometric sensor, such as wireless or mobile communication apparatuses (for example smartphones and tablet computers), e-book readers and apparatuses included in a vehicle dashboard.

The illustrated apparatus 1000 includes a controller or a processor 1002 (i.e.—a signal processor, microprocessor, ASIC, or other control and processing logic circuitry) for performing such tasks as signal coding, data processing, input/output processing, power control, and/or other functions. An operating system 1004 controls the allocation and usage of the components of the apparatus 1000 and support for one or more application programs 1006. The application programs 1006 can include common mobile applications, for instance, telephony applications, email applications, calendars, contact managers, web browsers, messaging applications, or any other application.

The illustrated apparatus 1000 includes one or more memory components, for example, a non-removable memory 1008 and/or removable memory 1010. The non-removable memory 1008 can include RAM, ROM, flash memory, a hard disk, or other well-known memory storage technologies. The removable memory 1010 can include flash memory or smart cards. The one or more memory components can be used for storing data and/or code for running the operating system 1004 and the applications 1006. Example of data can include web pages, text, images, sound files, image data, video data, or other data sets to be sent to and/or received from one or more network servers or other devices via one or more wired or wireless networks. The electronic device 1000 may further include a subscriber identity module (SIM) 1012. The SIM 1012 typically stores information elements related to a mobile subscriber. A SIM is well known in Global System for Mobile Communications (GSM) communication systems, Code Division Multiple Access (CDMA) systems, or with third-generation (3G) wireless communication protocols such as Universal Mobile Telecommunications System (UMTS), CDMA1000, wideband CDMA (WCDMA) and time division-synchronous CDMA (TD-SCDMA), or with fourth-generation (4G) wireless communication protocols such as LTE (Long-Term Evolution).

The apparatus 1000 can support one or more input devices 1020 and one or more output devices 1030. Examples of the input devices 1020 may include, but are not limited to, a touchscreen 1022 (i.e., capable of capturing finger tap inputs, finger gesture inputs, multi-finger tap inputs, multi-finger gesture inputs, or keystroke inputs from a virtual keyboard or keypad), a microphone 1024 (i.e., capable of capturing voice input), a camera module 1026 (i.e., capable of capturing still picture images and/or video images) and a physical keyboard 1028. Examples of the output devices 1030 may include, but are not limited to a speaker 1032 and a display 1034. Other possible output devices (not shown) can include piezoelectric or other haptic output devices. Some devices can serve more than one input/output function. For example, the touchscreen 1022 and the display 1034 can be combined into a single input/output device. The display 1034 may include any of the display units of FIG. 1-FIG. 9. The touchscreen 1022 may include any of the touch screen layers of FIG. 1-FIG. 9.

In an embodiment, the apparatus 1000 may comprise a wireless radio(s) 1040. The wireless radio(s) 1040 can support two-way communications between the processor 1002 and external devices, as is well understood in the art. The wireless radio(s) 1040 are shown generically and can include, for example, a cellular modem 1042 for communicating at long range with the mobile communication network, a Wi-Fi radio 1044 for communicating at short range with a local wireless data network or router, and/or a Bluetooth radio 1046. The cellular modem 1042 is typically configured for communication with one or more cellular networks, such as a GSM/3G/4G network for data and voice communications within a single cellular network, between cellular networks, or between the mobile device and a public switched telephone network (PSTN).

The apparatus 1000 can further include one or more input/output ports 1050, a power supply 1052, one or more sensors 1054, for example an accelerometer, a gyroscope, a compass, or an infrared proximity sensor for detecting the orientation or motion of the electronic device 1000, and a transceiver 1056 (for wirelessly transmitting analog or digital signals). The illustrated components are not required or all-inclusive, as any of the components shown can be deleted and other components can be added.

Computer executable instructions may be provided using any computer-readable media that is accessible by computing based devices. Computer-readable media may include, for example, computer storage media such as memory and communications media. Computer storage media, such as memory includes volatile and non-volatile, removable and non-removable media implemented in any method or technology for storage of information such as computer readable instructions, data structures, program modules or other data. Computer storage media includes, but is not limited to, RAM, ROM, EPROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device. In contrast, communication media may embody computer readable instructions, data structures, program modules, or other data in a modulated data signal, such as a carrier wave, or other transport mechanism. As defined herein, computer storage media does not include communication media. Therefore, a computer storage medium should not be interpreted to be a propagating signal per se. Propagated signals may be present in a computer storage media, but propagated signals per se are not examples of computer storage media. Although the computer storage media is shown within the computing based devices it will be appreciated that the storage may be distributed or located remotely and accessed via a network or other communication link, for example by using a communication interface.

At least some of the examples disclosed in FIGS. 1-10 are able to provide a biometric sensor integrated with a controller chip. At least some of the examples disclosed in FIGS. 1-10 are able to provide reduced space requirements for device implementation. At least some of the examples disclosed in FIGS. 1-10 are able to provide less complex device implementation. At least some of the examples disclosed in FIGS. 1-10 are able to provide reduced costs for device implementation. At least some of the examples disclosed in FIGS. 1-10 are able to provide a reduced number of external connectors due to the signals from/to the biometric sensor being routed via the conductive adhesive layer and the conductive bonding points in connection with the associated controller rather than via an external connector.

An embodiment of a display unit comprises a display panel configured to display digital images; an at least partially transparent protective layer arranged above the display panel; and a controller communicatively attached onto an upper surface of the display panel, wherein a biometric sensor pattern is integrated in the controller, and the controller is configured to control the biometric sensor pattern.

In an embodiment, alternatively or in addition to the above described embodiments, the controller is further configured to control the display panel.

In an embodiment, alternatively or in addition to the above described embodiments, the display unit further comprises a touch screen layer arranged above the display panel, and the controller is further configured to control at least one of the display panel and the touch screen layer.

In an embodiment, alternatively or in addition to the above described embodiments, the at least partially transparent protective layer comprises a recess in its lower surface configured to receive the controller at least partly.

In an embodiment, alternatively or in addition to the above described embodiments, the controller is arranged below the at least partially transparent protective layer.

In an embodiment, alternatively or in addition to the above described embodiments, the controller is attached to the lower surface of the at least partially transparent protective layer via an adhesive layer arranged between the lower surface of the at least partially transparent protective layer and an upper surface of the controller.

In an embodiment, alternatively or in addition to the above described embodiments, the display unit further comprises an optically clear layer arranged at least between the lower surface of the at least partially transparent protective layer and an upper surface of the controller.

In an embodiment, alternatively or in addition to the above described embodiments, the display unit further comprises an optically clear layer arranged between the at least partially transparent protective layer and the display panel.

In an embodiment, alternatively or in addition to the above described embodiments, the biometric sensor pattern comprises at least one of a fingerprint sensor pattern and a pulse sensor pattern.

In an embodiment, alternatively or in addition to the above described embodiments, the biometric sensor pattern is integrated one of: on the upper surface of the controller and at least partly inside the upper surface of the controller.

In an embodiment, alternatively or in addition to the above described embodiments, the controller is communicatively attached onto the upper surface of the display panel via at least one of: a conductive adhesive layer arranged between the upper surface of the display panel and a lower surface of the controller, and multiple conductive bonding points arranged on the lower surface of the controller.

In an embodiment, alternatively or in addition to the above described embodiments, the controller and the biometric sensor pattern comprise semiconductor material.

In an embodiment, alternatively or in addition to the above described embodiments, the display unit comprises one of: a liquid-crystal display unit, an organic light-emitting diode display unit, and an electrophoretic ink display unit.

An embodiment of an electronic device comprises a printed circuit board and a display unit arranged at least partly above the printed circuit board. The display unit comprises a display panel configured to display digital images; an at least partially transparent protective layer arranged above the display panel; and a controller communicatively attached onto an upper surface of the display panel, wherein a biometric sensor pattern is integrated in the controller, and the controller is configured to control the biometric sensor pattern.

In an embodiment, alternatively or in addition to the above described embodiments, the controller is further configured to control the display panel.

In an embodiment, alternatively or in addition to the above described embodiments, the display unit further comprises a touch screen layer arranged above the display panel, and the controller is further configured to control at least one of the display panel and the touch screen layer.

In an embodiment, alternatively or in addition to the above described embodiments, the biometric sensor pattern comprises at least one of a fingerprint sensor pattern and a pulse sensor pattern.

In an embodiment, alternatively or in addition to the above described embodiments, the controller is communicatively attached onto the upper surface of the display panel via at least one of: a conductive adhesive layer arranged between the upper surface of the display panel and a lower surface of the controller, and multiple conductive bonding points arranged on the lower surface of the controller.

In an embodiment, alternatively or in addition to the above described embodiments, the controller and the biometric sensor pattern comprise semiconductor material.

An embodiment of a sensor controller comprises a body comprising semiconductor material; and a biometric sensor pattern comprising semiconductor material and integrated in the body of the controller, wherein the controller is configured to control the biometric sensor pattern.

The term 'computer' or 'computing-based device' is used herein to refer to any device with processing capability such that it can execute instructions. Those skilled in the art will realize that such processing capabilities are incorporated into many different devices and therefore the terms 'computer' and 'computing-based device' each include mobile telephones (including smart phones), tablet computers and many other devices.

The processes described herein may be performed by software in machine readable form on a tangible storage medium e.g. in the form of a computer program comprising computer program code means adapted to perform all the steps of any of the processes described herein when the program is run on a computer and where the computer program may be embodied on a computer readable medium. Examples of tangible storage media include computer storage devices comprising computer-readable media such as disks, thumb drives, memory etc. and do not include propagated signals. Propagated signals may be present in a tangible storage media, but propagated signals per se are not examples of tangible storage media. The software can be suitable for execution on a parallel processor or a serial processor such that the method steps may be carried out in any suitable order, or simultaneously.

This acknowledges that software can be a valuable, separately tradable commodity. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), and the like.

Any range or device value given herein may be extended or altered without losing the effect sought, as will be apparent to the skilled person.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims, and other equivalent features and acts are intended to be within the scope of the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

Aspects of any of the examples described above may be combined with aspects of any of the other examples described to form further examples without losing the effect sought.

The term 'comprising' is used herein to mean including the blocks or elements identified, but that such blocks or elements do not comprise an exclusive list, and a system, a device or an apparatus may contain additional blocks or elements.

It will be understood that the above description is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the spirit or scope of this specification. In particular, the individual features, elements, or parts described in the context of one example, may be connected in any combination to any other example also.

The invention claimed is:

1. A display unit, comprising:
   a display panel configured to display digital images;
   an at least partially transparent protective layer arranged above the display panel;
   a controller communicatively attached onto an upper surface of the display panel;
   a touch screen layer arranged above the display panel such the touch screen layer is between the display panel and the at least partially transparent protective layer; and
   a color filter arranged between the at least partially transparent protective layer and touch screen layer, the color filter being arranged aside the controller; and
   wherein a biometric sensor pattern is integrated inside an upper surface of the controller.

2. The display unit as claimed in claim 1, wherein the controller is attached to the lower surface of the at least partially transparent protective layer via an adhesive layer arranged between the lower surface of the at least partially transparent protective layer and an upper surface of the controller.

3. The display unit as claimed in claim 1, wherein the controller is configured to control one or more of the following: the display panel and the touch screen layer.

4. The display unit as claimed in claim 1, wherein a lower surface of the at least partially transparent protective layer completely covers an upper surface of the biometric sensor pattern and the upper surface of the display panel completely covers a lower surface of the controller such that the biometric sensor and the controller are arranged between the display panel and the at least partially transparent protective layer.

5. The display unit as claimed in claim 4, wherein a polarizer and the color filter are arranged aside the controller.

6. The display unit as claimed in claim 5, wherein the polarizer and the color filter are between the at least partially transparent protective layer and the touch screen layer.

7. The display unit as claimed in claim 1, wherein the controller is communicatively attached onto the upper surface of the display panel via one or more of: a conductive adhesive layer arranged between the upper surface of the display panel and a lower surface of the controller, and multiple conductive bonding points arranged on the lower surface of the controller.

8. The display unit as claimed in claim 1, wherein a polarizer is between the at least partially transparent protective layer and the touch screen layer.

9. The display unit as claimed in claim 1, wherein the controller and the biometric sensor pattern comprise semiconductor material.

10. An electronic device comprising a printed circuit board and a display unit arranged at least partly above the printed circuit board, the display unit comprising:
an outer surface;
a display panel configured to display digital images;
an at least partially transparent protective layer arranged above the display panel;
a controller directly attached onto an upper surface of the display panel;
a touch screen layer above the display panel such the touch screen layer is between the display panel and the at least partially transparent protective layer; and
a color filter arranged between the at least partially transparent protective layer and the touch screen layer, the color filer being arranged aside the controller; and
wherein a biometric sensor pattern is integrated inside an upper surface of the controller.

11. The electronic device as claimed in claim 10, wherein the biometric sensor pattern and the at least partially transparent protective layer form the outer surface.

12. The electronic device as claimed in claim 11, wherein the controller is communicatively attached onto the upper surface of the display panel via a conductive adhesive layer arranged between the upper surface of the display panel and a lower surface of the controller, and multiple conductive bonding points arranged on the lower surface of the controller.

13. The electronic device as claimed in claim 11, wherein the controller and the biometric sensor pattern comprise semiconductor material.

14. The electronic device as claimed in claim 11, wherein the controller is configured to control the biometric sensor pattern, the display panel, and the touch screen layer.

15. The electronic device as claimed in claim 14, wherein the controller is attached to the lower surface of the at least partially transparent protective layer via an adhesive layer arranged between the lower surface of the at least partially transparent protective layer and an upper surface of the controller.

16. A display unit, comprising:
a display panel configured to display digital images;
a protective layer arranged above the display panel;
a controller directly attached on a surface of the display panel;
a touch screen layer arranged above the display panel such the touch screen layer is between the display panel and the protective layer; and
a color filter arranged between the protective layer and the touch screen layer, the color filer being arranged aside the controller; and
wherein a biometric sensor pattern is integrated inside an upper surface of the controller.

17. The display unit as claimed in claim 16, wherein a polarizer and the color filter are between the at least partially transparent protective layer and the touch screen layer.

18. The display unit as claimed in claim 16, wherein a lower surface of the protective layer covers an upper surface of the biometric sensor pattern and an upper surface of the display panel covers a lower surface of the controller such that the biometric sensor and the controller are arranged between the display panel and the protective layer.

19. The display unit as claimed in claim 16, wherein the controller and the biometric sensor pattern comprise semiconductor material.

20. The display unit as claimed in claim 16, wherein the controller is attached to the lower surface of the protective layer via an adhesive layer arranged between the lower surface of the protective layer and an upper surface of the controller.

* * * * *